United States Patent
Skierski et al.

(10) Patent No.: US 7,116,420 B2
(45) Date of Patent: Oct. 3, 2006

(54) METHOD OF COLOR MATCHING WOOD STAINS

(75) Inventors: Thomas J. Skierski, Brunswick Hills, OH (US); Mohammed A. Aziz, Strongsville, OH (US); Thomas L. Cope, Lyndhurst, OH (US)

(73) Assignee: The Sherwin-Williams Company, Cleveland, OH (US)

( * ) Notice: Subject to any disclaimer, the term of this patent is extended or adjusted under 35 U.S.C. 154(b) by 504 days.

(21) Appl. No.: 10/713,675

(22) Filed: Nov. 14, 2003

(65) Prior Publication Data

US 2004/0131756 A1    Jul. 8, 2004

Related U.S. Application Data

(60) Provisional application No. 60/428,539, filed on Nov. 21, 2002.

(51) Int. Cl.
*G01N 21/25* (2006.01)
*C23C 14/5412* (2006.01)

(52) U.S. Cl. .......................... 356/408; 356/319; 427/8; 427/10; 427/258

(58) Field of Classification Search ............... 356/319, 356/300, 408, 421, 425, 402; 427/8, 10, 427/258
See application file for complete search history.

(56) References Cited

U.S. PATENT DOCUMENTS

| | | |
|---|---|---|
| 3,059,524 A | 10/1962 | Grassmann et al. ............ 88/14 |
| 3,368,864 A | 2/1968 | Gugerli ............................ 8/25 |
| 3,601,589 A | 8/1971 | McCarty ..................... 235/150 |
| 3,690,771 A | 9/1972 | Armstron, Jr. et al. ..... 356/176 |
| 3,758,842 A | 9/1973 | Kudlacik ..................... 322/25 |
| 4,093,991 A | 6/1978 | Christie, Jr. et al. ........ 356/525 |
| 4,887,217 A | 12/1989 | Sherman et al. ............ 364/468 |
| 5,003,500 A | 3/1991 | Gerber ....................... 364/526 |
| 5,116,408 A | 5/1992 | Crozer ........................ 106/19 |
| 5,231,472 A | 7/1993 | Marcus et al. .............. 356/402 |
| 5,387,977 A | 2/1995 | Berg et al. ................... 356/407 |
| 5,493,404 A | 2/1996 | Allaire et al. ............... 356/402 |
| 5,761,070 A | 6/1998 | Conners et al. ........ 364/478.11 |
| 5,933,578 A | 8/1999 | Van de Capelle et al. .. 395/109 |
| 6,166,814 A | 12/2000 | Pringle ....................... 356/445 |
| 6,287,377 B1 | 9/2001 | Binns et al. ................. 106/499 |
| 6,362,885 B1 | 3/2002 | Osumi et al. ............... 356/402 |

FOREIGN PATENT DOCUMENTS

WO   WO 02/082026 A1   10/2002

*Primary Examiner*—Layla G. Lauchman
(74) *Attorney, Agent, or Firm*—Vivien Y. Tsang; Robert E. McDonald; Paul R. Katterle

(57) ABSTRACT

A method of producing a finish for a selected wood substrate, wherein the finish provides the selected wood substrate with a color that matches the color of a target object. In accordance with the method, calculations are performed to determine the quantities of at least one group of colorants required to produce a semitransparent wood stain from a vehicle, wherein when the semitransparent wood stain is applied to the selected wood substrate, the selected wood substrate will have a color that matches the target object. The calculations are performed using reflectance measurements of the target object obtained using a spectrophotometer and previously obtained spectral data of the colorants as applied to at least one type of wood. The colorants used to form the semitransparent wood stain do not include a white colorant.

12 Claims, 1 Drawing Sheet

METHOD OF COLOR MATCHING WOOD STAINS

CROSS-REFERENCE TO RELATED APPLICATION

This application claims the benefit of U.S. provisional patent application No. 60/428,539 filed on Nov. 21, 2002, the entirety of which is hereby incorporated by reference.

BACKGROUND OF THE INVENTION

The present invention relates to color matching and, more specifically, to a computerized method of color matching semitransparent wood stains.

Stains are semitransparent solutions or suspensions of coloring matter (such as dyes or pigments or both) in a vehicle, designed to color a surface by penetration without hiding it or leaving a continuous film. In contrast, paints are opaque solutions or suspensions of coloring matter in a vehicle, designed to hide or cover a surface with an opaque film. Computerized color matching techniques using spectrophotometers are routinely used to color match paints. Heretofore, computerized color matching techniques using spectrophotometers have not been used to color match semitransparent stains, presumably because the substrate to be stained and/or the substrate of the stain standard to be matched are not hidden by the stains and are conventionally thought to effect the color of the stains in a manner that cannot be properly accounted for by conventional computerized color matching techniques. Instead, semitransparent stains are conventionally color matched using a trial-by-error method. In such a trial-by-error method, a colorist inspects the color of the stain standard and then guesses the pigments in a library and relative concentrations necessary to provide a color matching stain. A stain is then prepared based on the pigment and concentration guesses. The stain is applied to a substrate and then the stained substrate is compared to the stain standard. If the visual inspection indicates that the stain standard and the stained substrate do not match, the colorist guesses at the amount of pigments to add to the stain and the new stain is applied to the substrate. These steps are repeated until the colorist determines that there is a color match. As can be appreciated, such a trial-by-error method is tedious and relies upon the skill of the colorist for its effectiveness. Accordingly, there is a need in the art for a computerized method of color matching semitransparent stains. The present invention is directed to such a method.

SUMMARY OF THE INVENTION

In accordance with the present invention, a method is provided for producing a finish for a selected wood substrate, wherein the finish provides the selected wood substrate with a color that matches the color of a target object. The method includes the steps of providing a spectrophotometer, providing a plurality of different colorants, wherein none of the colorants are a white colorant, providing a vehicle for producing semitransparent wood stain and providing at least one database containing spectral data for the colorants as applied to at least one type of wood. Reflectance measurements of the target object are obtained using the spectrophotometer. Calculations are performed to determine the quantities of at least one group of the colorants required to produce a semitransparent wood stain from the vehicle, wherein when the semitransparent wood stain is applied to the selected wood substrate, the selected wood substrate will have a color that matches the target object. The calculations are performed using the spectral data of the colorants and the reflectance measurements of the target object. The semitransparent stain is produced from the vehicle and the at least one group of colorants. A portion of the selected wood substrate is stained with the semitransparent wood stain and reflectance measurements of the stained portion of the selected wood substrate are obtained using the spectrophotometer. A determination is made whether the color of the stained portion of the selected wood substrate is within a certain color tolerance of the color of the target object. The determination is made using the reflectance measurements of the target object and the reflectance measurements of the stained portion of the selected wood substrate.

BRIEF DESCRIPTION OF THE DRAWINGS

The features, aspects, and advantages of the present invention will become better understood with regard to the following description, appended claims, and accompanying drawings where:

DETAILED ESCRIPTION OF THE PREFERRED EMBODIMENTS

Figure 1:
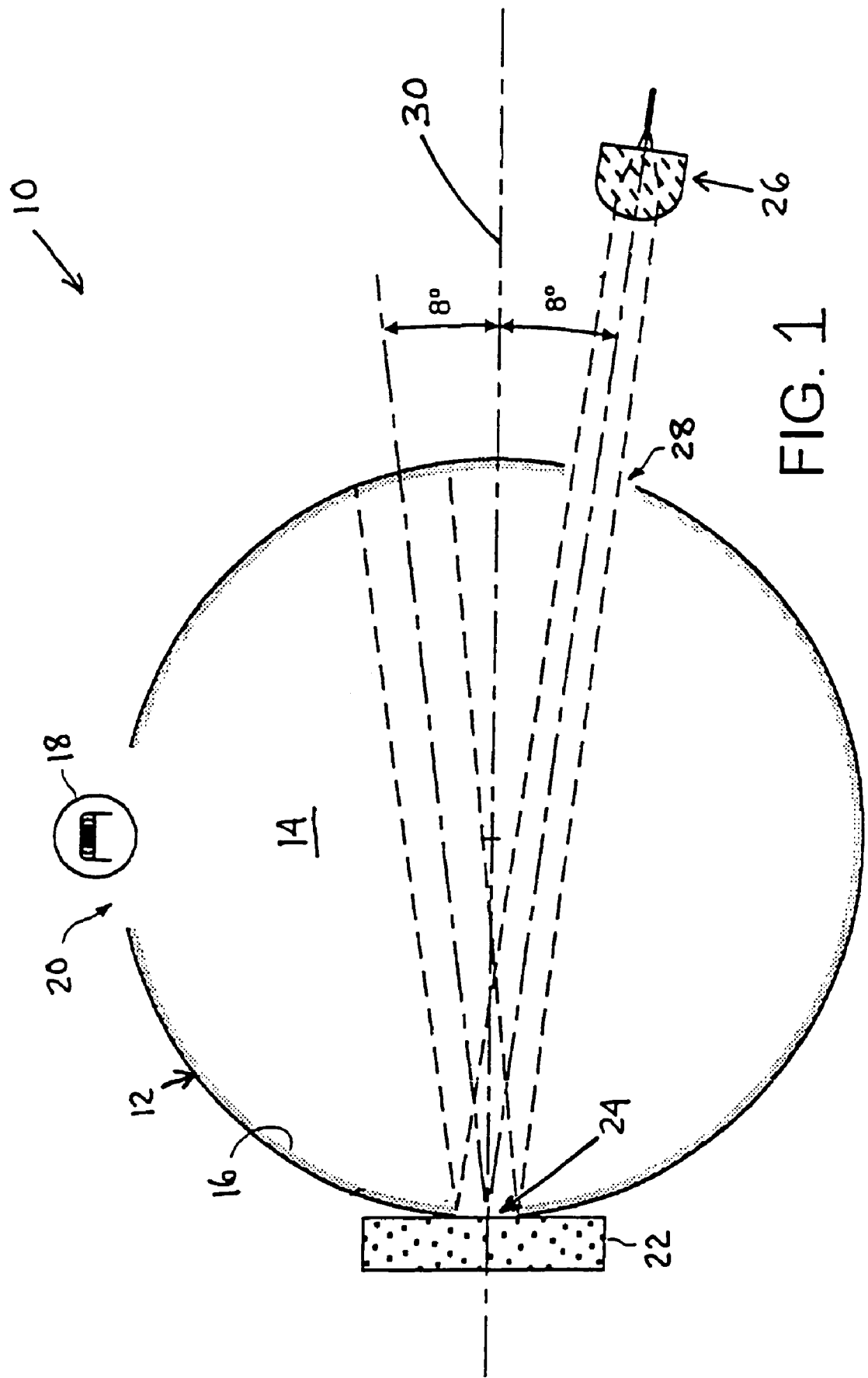
FIG. 1 is a schematic view of a portion of a single angle spectrophotometer for use in the method of the present invention.

As used herein, the term "wood stain" shall mean a semitransparent solution or suspension of coloring matter (such as dyes or pigments or both) in a vehicle (binder and thinner), designed to color a piece of wood by penetration without hiding it or leaving a continuous film. Wood stains have low solids contents relative to paint, i.e., frequently less than 20 percent by weight solids.

Wood stains can be oil-based or water-based. Oil-based wood stains generally comprise one or more pigments, a binder such as an alkyd resin containing a drier, and organic solvents such as mineral spirits, VMP naphtha, kerosene, xylene, toluene or a mixture of these. In contrast, water-based wood stains have waterborne binders such as acrylic emulsions and water dilutable alkyds.

As used herein, the term "vehicle" shall mean a binder and one or more thinners and optionally other ingredients (excluding colorants) used to form wood stains.

As used herein, "colorant" shall mean a substance that imparts color to another material or mixture. Colorants can be either dyes or pigments (organic or inorganic). Pigments are insoluble in the vehicle, whereas dyes are soluble in the vehicle. Inorganic pigments include metal oxides such as the oxides of iron, titanium, zinc, cobalt, and chrome. Earth pigments may utilize mineral pigments obtained from clay. Various forms of carbon may be used for black pigments. Organic pigments are insoluble in the vehicle and are derived from natural or synthetic materials, and include phthalocyanine, lithos, toluidine, and para red. Organic pigments may be employed in a precipitated form as a lake. Dyes are organic materials and include acid dyes, such as azo, diazo and triarylmethane dyes, and basic dyes, such as aniline dyes.

Pigment-based colorants are often provided in the form of tinting concentrates comprising highly concentrated levels of color pigment dispersed into a vehicle. The amount of color pigment used in a colorant is typically from about 5 weight percent to about 70 weight percent, depending on the type of color pigment.

As used herein the term "chromatic colorant" shall mean a colorant that is not black, white or grey.

The present invention is directed to a method of color matching wood stains. More specifically, the present invention is directed to a method of producing a wood stain that when applied to a desired wood substrate will have the same or substantially the same color as a target object, taking into account clear topcoats or other finishes on the target object and/or the desired object. The method of the present invention may be used for both oil-based and water-based wood stains.

The method utilizes a single angle spectrophotometer 10 connected to a personal computer with a central processing unit. The computer runs a color matching software program that is proprietary to the assignee of the present invention, namely The Sherwin-Williams Company. As will be described more fully below, the color matching software program includes a plurality of databases containing spectral data for colorants applied to different wood substrates. The color matching software program also contains one or more formula(s) for wood stain composition(s) (ex colorants) describing the required proportions of vehicle and other additives.

As shown in FIG. 1, the spectrophotometer 10 may have an integrating sphere 12 defining a cavity 14 with a highly reflective, optically diffuse surface 16. A light source 18 connected to the cavity 14 via a lamp port 20 illuminates the cavity 14 to diffusely illuminate a specimen 22 at a specimen port 24. A receiver 26 is positioned at a receiver port 28 to receive optical radiation from the specimen 22. The receiver 26 may be positioned normal to the specimen 22, along the diameter of the sphere 12, or, more preferably, at angle of up to 10°, more preferably about 8° from the specimen normal 30. The receiver 26 conveys the reflected light from the specimen 22 to a light analyzer (not shown). The light analyzer also receives reference light from the light source, which is used to correct for variations in the intensity of the light source. The light analyzer includes a device for separating light into its component wavelengths, such as a diffraction grading or a prism, and an array of detectors to measure the intensities of the different wavelengths. Signals from the detector array are multiplexed and fed to a data processor (not shown), which produces digital signals that are conveyed to the personal computer.

A commercially-available single angle spectrophotometer that may be used in the present invention is the ColorEye 7000 color spectrophotometer sold by Gretag Macbeth.

The present invention utilizes a collection or library of different colorants. The colorant library include a black colorant, a white colorant and a plurality of chromatic colorants. As will be described more fully below, the white colorant is used to determine the spectral characteristics of the other colorants, but the white colorant is not used to formulate the batch wood stain that is being produced to match a target object. In one embodiment of the present invention, the library of colorants comprises fifteen different colorants, including the black colorant and the white colorant.

First, the spectral characteristics of the colorants (as applied to certain catalogued wood substrates) are determined and stored in the computer databases. The spectral characteristics of the colorants are determined from reflectance measurements using the Kubelka-Munk Theory. As is well known, the Kubelka-Munk Theory relates reflectance at complete hiding ($R\infty$) of a paint film at a specific wavelength to two optical constants, K (the absorption coefficient) and S (the scattering coefficient). After some basic assumptions, the Kubelka-Munk Theory can be expressed by the following equation:

$$\frac{K}{S} = \frac{(1-R\infty)^2}{2R\infty} \quad \text{[equation 1]}$$

One of the assumptions behind the Kubelka-Munk equation that is not valid is that there is no reflection on the upper surface of the film. This is not possible because of the refractive index difference at the air/paint film interface. This invalid assumption, however, can be accounted for by using the Saunderson correction:

$$R_m = k_1 + (1-k_1)(1-k_2)\frac{R}{1-k_2 R} \quad \text{[equation 2]}$$

where
  $R_m$=measured reflectance
  R=true Kubelka-Munk reflectance
  $k_1$=external reflectance coefficient
  $k_2$=internal reflectance coefficient An important aspect of the Kubelka-Munk Theory is that the absorption coefficients and the scattering coefficients are additive quantities. For a paint film where i denotes the ith component of a mixture of N colorants and where $C_i$ is the concentration of the ith colorant, the absorption and scattering coefficients of the mixture are:

$$K = \sum_{i=1}^{N} C_i K_i \quad \text{[equations 3a]}$$

$$S = \sum_{i=1}^{N} C_i S_i \quad \text{[equation 3b]}$$

Also:

$$\frac{K}{S} = \frac{\sum_{i=1}^{N} C_i K_i}{\sum_{i=1}^{N} C_i S_i} \quad \text{[equation 4]}$$

Although the Kubelka-Munk Theory was developed for paints and the foregoing equations presume complete hiding of the underlying substrate, Applicants have surprisingly found that the Kubelka-Munk Theory and the foregoing equations can be used for color matching stained wood substrates. In essence, the stained wood substrates are assumed to be the paint films for purposes of the equations.

The catalogued wood substrates that are used to determine the spectral characteristics of the colorants preferably include panels composed of different types of woods. Preferably, panels composed of at least maple, red oak and cherry are used. Additional panels composed of other types of wood, such as ash, white pine and black walnut, may also be used. All of the panels are sanded to have smooth, even surfaces.

Each of the chromatic colorants is mixed with the white colorant in a vehicle to form a plurality of binary white characterization mixtures. For each of the white characterization mixtures, the white colorant is added to a mixture of the vehicle and the chromatic colorant until the mixture has a reflectance greater than 25% at the peak absorption point of the mixture's spectral curve. The concentration of the white colorant $C_{wh}$ and the concentration of the chromatic colorant $C_{ci}$ are noted and recorded for each of the white characterization mixtures.

Each of the chromatic colorants is mixed with the black colorant in a vehicle to form a plurality of binary black characterization mixtures. For each of the black characterization mixtures, the chromatic colorant is added to a mixture of the vehicle and the black colorant until the chromatic colorant just becomes visible. The concentration of the black colorant $C_{bk}$ and the concentration of the chromatic colorants $C_{ci}$ are noted and recorded.

Black and white masstones are formed in vehicles from the black and white colorants, respectively. In addition the black colorant is mixed with the white colorant in a vehicle to form a black-white characterization mixture, wherein the white colorant is added to a mixture of the vehicle and the black colorant until the mixture has a reflectance greater than 25% at the peak absorption point of the mixture's spectral curve. The concentration of the black colorant $C_{bk}$ and the concentration of the white colorant $C_{wh}$ for the black-white characterization mixture are noted and recorded.

Preferably, the vehicles that are used to form the white masstone, the black masstone, the black-white characterization mixture, the white characterization mixtures, the black characterization mixtures and the batch wood stain(s) produced from color matching (as described below) are the same. In this manner, the effect of the vehicle on the color of the wood substrates is taken into account.

The white masstone, the black masstone, the black-white characterization mixture, the white characterization mixtures, and the black characterization mixtures are applied to maple wood panels, cherry wood panels and red oak panels, with each composition being applied to a dedicated maple wood panel, a dedicated cherry wood panel and a dedicated red oak panel. The wood panels with the compositions applied thereto are allowed to dry. Reflectance readings of the dried panels are then made using the spectrophotometer 10. On each wood panel, readings at four different locations are made. Two readings are made in two different light wood areas, e.g. sapwood areas, and two readings are made in two different darker wood areas, e.g. heartwood areas. Readings are not made in knot areas or other areas containing defects. Each reading comprises a plurality of reflectance measurements made at 10 to 20 nanometer intervals along the visible light spectrum, which extends from about 400 nanometers to about 700 nanometers. The reflectance measurements of the four readings at each wavelength interval are averaged to produce average reflectance measurements.

For each type of catalogued wood substrate, the average reflectance measurements for the white masstone, the black-white characterization mixture and the black masstone are used to calculate the K and S values for the white colorant and the black colorant for the catalogued wood substrate by solving the equations set forth above, wherein equation 1 with the correction of equation 2 is used for the black masstone and the white masstone and wherein equations 1 and 4 (with the correction of equation 2) are used for the black characterization mixture, with the concentration of the black colorant $C_{bk}$ and the concentration of the white colorant $C_{wh}$ being used for $C_i$. Thus, if three different types of wood panels are used, such as maple, cherry and red oak, three different sets of K and S values for the white colorant are determined and three different K and S values for the black colorant are determined. These K and S values are stored in a database of the color matching software program that is run on the personal computer.

For each chromatic colorant for each type of wood panel, the average reflectance measurements for its white characterization mixture and its black characterization mixture are used to calculate the K and S values for the chromatic colorant by solving equations 1 and 4 (with the correction of equation 2) for the white characterization mixture and the black characterization mixture, with the concentration of the black colorant $C_{bk}$, the concentration of the white colorant $C_{wh}$ and the concentration of the chromatic colorant $C_{ci}$ being used for $C_i$. These K and S values are stored in the database of the color matching software program.

The database of the color matching software program is divided into a plurality of sub-databases, with each sub-database containing the K and S values for a particular catalogued wood substrate. Thus, there are preferably at least three sub-databases, one for the maple substrate, one for the red oak substrate and one for the cherry substrate.

Once the spectral characteristics (i.e., the K and S values) of the black colorant, the white colorant and the chromatic colorants for the catalogued wood substrates have been determined and entered into the databases of the color matching software program, the spectrophotometer 10 and the color matching software program may be used to formulate a batch of wood stain that when applied to a bare wood sample substrate and provided with a particular finish will have a color matching a target object.

First, a colorist inspects the bare wood sample substrate to determine the type of wood the bare wood sample substrate is composed of. If necessary, the colorist will sand the bare wood substrate to ensure it is substantially smooth. Preferably, the bare wood sample substrate is the same type of wood as the wood substrate of the target object. The colorist also inspects the target object to see if it is covered with a clear topcoat or other type of finish. Once this information is ascertained, the colorist selects the catalogued wood substrate that is the same as, or closest to, the wood of the bare wood sample substrate.

The colorist calls up a wood stain formula (ex colorants) and enters the amount of batch wood stain that is desired into the color matching software program. The colorist then instructs the color matching software program to access the spectral data (K and S values) stored in the database for the selected catalogued wood substrate when the color matching software program performs the color matching calculations set forth below. The called-up wood stain formula (ex colorants) together with the colorants (and amounts thereof) calculated by the color matching software program are hereinafter collectively referred to as the batch wood stain formula.

Reflectance readings of the target object are then made using the spectrophotometer 10. Using the same method employed during the formation of the database, reflectance readings of the target object at four different locations are made. Two readings are made in two different light wood areas, e.g. sapwood areas, and two readings are made in two different darker wood areas, e.g. heartwood areas. Once again, readings are not made in knot areas or other areas containing defects. Each reading comprises a plurality of reflectance measurements made at 10 to 20 nanometer intervals along the visible light spectrum. The reflectance measurements of the four readings at each wavelength interval are averaged to produce average reflectance measurements. Using these average reflectance measurements, the X, Y and Z tristimulus values for the target object are calculated based on this data according to the formulas:

$$X = \sum_\lambda ER_x$$

$$Y = \sum_\lambda ER_y$$

$$Z = \sum_\lambda ER_z$$

where E is the relative energy of a standard light source, R is the average reflectance of the target object and x, y, z are the color mixture functions for a specified observer. The amount of the colorants that must be added to provide the batch wood stain with a color falling within the color tolerance value is determined based on mathematical calculations run by the color matching software program in the personal computer.

The mathematical procedure utilized to calculate the amount of the colorants to be added based upon a difference in X, Y and Z readings are well known in the art. A particularly useful procedure is that described in Eugene Allen's article in the Journal of the Optical Society of America, Volume 64, Number 7, July 1974 pages 991 to 993 the teaching of which is hereby incorporated by reference. A procedure based on Eugene Allen's method (similar to the one used herein) is described in U.S. Pat. No. 4,887,217 to Sherman et al., which is assigned to the assignee of the present application and which is hereby incorporated by reference. For a colorant having a given concentration, absorption coefficient and scattering coefficient, this procedure provides a determination of the amount of said colorant which must be added to adjust the X, Y, Z readings from one value to another.

In a preferred application of the Eugene Allen color matching procedure, a mathematical technique is first applied to the batch wood stain in a prediction stage to determine, by an iterative process, the quantities of the colorants that must be added to the batch wood stain to theoretically match the X, Y and Z values of the target object. In a correction stage, the mathematical technique is again applied in an iterative process to determine the amount (if any) of the colorants necessary to move from the color of the produced batch wood stain to the desired color of the target object.

In the color matching procedure of the present invention, 3 or 4 colorant formulas are typically produced. If, however, the target object has a difficult to match color, such as a violet color, a very saturated dark color, or a highly chromatic color, a 5 colorant formula may be specified. Importantly, the white colorant is not used in the color matching. The black colorant is also preferably forced out of the color matching, depending on the color of the target object.

The mathematical equations used in the color matching procedure of the present invention are set forth below. The equations assume four colorants are charged into the batch wood stain being produced and subsequently shading with three of the colorants.

$$c = \text{pigment concentration vector}_a = \begin{bmatrix} C_1 \\ C_2 \\ C_3 \end{bmatrix}_b$$

$$= (TE\{\underline{D_k \phi_k} - k^{(4)}u] + D_s[\phi_s - s^{(4)}u]\})^{-1} \cdot$$

$$C \underline{TE}\{D_k(k^{(a)} - k^{(4)}] + D_s[s^{(4)} - s^{(4)}]\}$$

where $$T = \begin{bmatrix} X_{400} & X_{420} & \cdots & X_{700} \\ X_{400} & X_{420} & \cdots & X_{700} \\ X_{400} & X_{420} & \cdots & X_{700} \end{bmatrix} = \begin{array}{l} \text{color mixture function for a} \\ \text{specified observer (available} \\ \text{from published references)} \end{array}$$

$$E = \begin{bmatrix} E_{400} & 0 & \cdots & 0 \\ 0 & E_{420} & \cdots & 0 \\ \cdots & \cdots & \cdots & \cdots \\ 0 & 0 & \cdots & E_{700} \end{bmatrix} = \begin{array}{l} \text{relative spectral energy} \\ \text{distribution of a specified} \\ \text{light source (available} \\ \text{from published references)} \end{array}$$

$$D_k = \begin{bmatrix} \left(\frac{\partial R}{\partial K}\right)_{400} & 0 & \cdots & 0 \\ 0 & \left(\frac{\partial R}{\partial K}\right)_{420} & \cdots & 0 \\ \cdots & \cdots & \cdots & \cdots \\ 0 & 0 & \cdots & \left(\frac{\partial R}{\partial K}\right)_{700} \end{bmatrix} = \begin{array}{l} \text{matrix describing partial} \\ \text{derivative of reflectance} \\ \text{with respect to absorbance} \\ \text{at each wavelength} \end{array}$$

where $\left(\frac{\partial R}{\partial K}\right)_i = -2R_i^{2/}[S_i(1-R_i^2)]$ $R_i$ = reflectance of color at $i$ $S_i$ = scattering of color at $i$ $$D_s = \begin{bmatrix} \left(\frac{\partial R}{\partial S}\right)_{400} & 0 & \cdots & 0 \\ 0 & \left(\frac{\partial R}{\partial S}\right)_{420} & \cdots & 0 \\ \cdots & \cdots & \cdots & \cdots \\ 0 & 0 & \cdots & \left(\frac{\partial R}{\partial S}\right)_{700} \end{bmatrix} = \begin{array}{l} \text{matrix describing partial} \\ \text{derivative of reflectance} \\ \text{with respect to scattering} \\ \text{at each wavelength} \end{array}$$

where $\left(\frac{\partial R}{\partial S}\right)_i = R_i(1-R_i)/[S_i(1+R_i)]$ $$\phi_k = \begin{bmatrix} K_{400}^{(1)} & K_{400}^{(2)} & K_{400}^{(3)} \\ K_{420}^{(1)} & K_{420}^{(2)} & K_{420}^{(3)} \\ \cdots & \cdots & \cdots \\ K_{700}^{(1)} & K_{700}^{(2)} & K_{700}^{(3)} \end{bmatrix} = \begin{array}{l} \text{absorption coefficient of the three colorants} \\ \text{(from the colorant characterization} \\ \text{procedure described above)} \end{array}$$

$$\phi_s = \begin{bmatrix} S_{400}^{(1)} & S_{400}^{(2)} & S_{400}^{(3)} \\ S_{420}^{(1)} & S_{420}^{(2)} & S_{420}^{(3)} \\ \cdots & \cdots & \cdots \\ S_{700}^{(1)} & S_{700}^{(2)} & S_{700}^{(3)} \end{bmatrix} = \begin{array}{l} \text{scattering coefficient of the three colorants} \\ \text{(from the colorant characterization} \\ \text{procedure described above)} \end{array}$$

$$k^{(4)} = \begin{bmatrix} K_{400}^{(4)} \\ K_{420}^{(4)} \\ \vdots \\ K_{700}^{(4)} \end{bmatrix} \quad s^{(4)} = \begin{bmatrix} S_{400}^{(4)} \\ S_{420}^{(4)} \\ \vdots \\ S_{700}^{(4)} \end{bmatrix} \quad u = [1\ 1\ 1]$$

where $S_i^{(a)} = \phi_s c + s^{(4)}(1 - C_1 - C_2 - C_3)$ $K_i^{(a)} = S_i^{(a)}(1-R_i)^2/2R_i$ $\Delta c = (TE\{D_k[\phi_k - k^{(4)}u] + D_s[\phi_s - s^{(4)}u]\})^{-1}\Delta t$ where $\Delta t$ is a vector $$\begin{bmatrix} \Delta X \\ \Delta Y \\ \Delta Z \end{bmatrix}$$

Representing the differences between the calculated batch wood stain X, Y and Z values and the X, Y and Z values of the target object.

$$R_i^{(a)} = \frac{1}{1 + \left(\frac{K_i^{(a)}}{S_i^{(a)}}\right) + \sqrt{\left(\frac{K_i^{(a)2}}{S_i^{(a)2}}\right) + 2\left(\frac{K_i^{(a)}}{S_i^{(a)}}\right)}}$$

These equations are conveniently utilized in the following manner:

A. As a first step, a rough color match of the target object is calculated, then an iterative calculation corrects the rough match to correspond to the target object colors by:

(1) Forming matrices T, E, u, $\phi_k$, $\phi_s$, k(4) and s(4);

(2) Calculate a rough match to the target object by calculating $K_i^{(a)}$ and $S_i^{(a)}$ from the batch wood stain formula;

(3) Utilize these $K_i^{(a)}$ and $S_i^{(a)}$ values to calculate $R_i^{(a)}$;

(4) Utilizing these values calculate the c matrix;

(5) Calculate $\Delta E$ according to the Friele-MacAdam-Chickering color difference equation:

$$\Delta E = [(\Delta C_{FMC})^2 + \Delta L^2]^{1/2}$$

Where:

$$\Delta C_{FMC} = K_1 \Delta C_1, \text{ and } \Delta L = K_2 \Delta L_2$$

$$\Delta C_1 = [(\Delta C_{rg}/a)^2 + (\Delta C_{yb}/b)^2]^{1/2}$$

$$\Delta L_1 = (P\Delta P + Q\Delta Q)/(P^2 + Q^2)^{1/2}$$

$$\Delta C_{rg} = (Q\Delta P - P\Delta Q)/(P^2 + Q^2)^{1/2}$$

$$\Delta Cyb = S\Delta L_1/(P^2 + Q^2)^{1/2} - \Delta S$$

$$\Delta L_2 = 0.279 \Delta L_1/a$$

$$K1 = 0.55669 + 0.49434Y - 0.825575 \cdot 10^{-3} Y^2 + 0.79172 \cdot 10^{-5} Y^3 - 0.30087 \cdot 10^{-7} Y^4,$$

$$K2 = 0.17548 + 0.027556Y - 0.57262 \cdot 10^{-3} Y^2 + 0.63893 \cdot 10^{-5} Y^3 - 0.26731 \cdot 10^{-7} Y^4,$$

$$a^2 = 17.3 \cdot 10^{-6} (P^2 + Q^2)/[1 + (2.73 P^2 Q^2)(P^4 + Q^4),$$

$$b^2 = 3.098 \cdot 10^{-4} (S^2 + 0.2015 Y^2)$$

$$P = 0.724X + 0.382Y - 0.098Z$$

$$Q = -0.48X + 1.37Y + 0.1276Z$$

$$S = 0.686Z$$

where:

$$\Delta P = 0.724(X_{rm} - X_{dt}) + 0.382(Y_{rm} - Y_{dt}) - 0.098(Z_{rm} - Z_{dt})$$

$$\Delta Q = -0.48(X_{rm} - X_{dt}) + 0.382(Y_{rm} - Y_{dt}) + 0.1276(Z_{rm} - Z_{dt})$$

$$\Delta S = 0.686(Z_{rm} - Z_{dt})$$

where the subscript rm identifies the tristimulus readings of the rough match and the subscript dt identifies the target object tristimulus values.

(6) If $\Delta E$ is sufficiently small, e.g. less than or equal to 0.1, no further iteration is necessary. If not, then iterate by generating the new values of $K_i$, $S_i$ and $R_i$ and calculate the tristimulus values of this new match t=TER and again calculate $\Delta E$. This process can be repeated until $\Delta E$ is sufficiently small.

(7) The rough match generated in steps (1)–(6) correlates the calculated color of the batch wood stain versus the tristimulus values of the target object. This is then iterated further to provide a closer match to the target object values by calculating a new $D_k$ and $D_s$ matrix from the newly generated values of $K_i$, $S_i$ and $R_i$. The new $D_k$ and $D_s$ matrices generate a new matrix to be inverted for the $\Delta C$ calculation. The new C matrix is calculated and corrected by the $\Delta C$ matrix so that $C_{new} = C_{old} + \Delta C$. These iterations can be repeated until $\Delta E$ is sufficiently small.

The color matching software program runs the foregoing equations for all four-colorant combinations of the colorants in the colorant library, excluding the white colorant and also preferably excluding the black colorant (depending on the color of the target object). Therefore, the color matching software program produces a number of different colorant formulations, with the white colorant (and also preferably the black colorant) being absent from each formulation. One of the colorant formulations is selected. This selection can be based on lowest cost, least metameric and/or lowest $\Delta E$.

B. Using the batch wood stain formula in the computer with the calculated amount of colorants required by the selected colorant formulation, a batch of wood stain is produced. The wood stain batch is applied to the bare wood sample substrate. If the target object is determined to have a clear topcoat, a clear top coat is applied to the sample substrate, over the region stained with the wood stain batch. Preferably, the sample substrate is allowed to dry. Reflectance readings of the sample substrate are then made using the spectrophotometer 10. Using the same method employed during the formation of the database, reflectance readings of the sample substrate at four different locations are made. Two readings are made in two different light wood areas, e.g. sapwood areas, and two readings are made in two different darker wood areas, e.g. heartwood areas. Once again, readings are not made in knot areas or other areas containing defects. Each reading comprises a plurality of reflectance measurements made at 10 to 20 nanometer intervals along the visible light spectrum. The reflectance measurements of the four readings at each wavelength interval are averaged to produce average reflectance measurements.

Based on the average reflectance measurements from the sample substrate, a determination is made (based on $\Delta E$) whether the color of the sample substrate is close enough to the target object. If the color of the sample substrate is not close enough to the color of the target object, the steps of (1)–(7) can then be repeated in the correction stage to re-determine the amount of the colorants needed to produce a second batch of the wood stain having a color that matches the color of the target object (within an acceptable $\Delta E$).

While the invention has been shown and described with respect to particular embodiments thereof, those embodiments are for the purpose of illustration rather than limitation, and other variations and modifications of the specific embodiments herein described will be apparent to those skilled in the art, all within the intended spirit and scope of the invention. Accordingly, the invention is not to be limited in scope and effect to the specific embodiments herein described, nor in any other way that is inconsistent with the extent to which the progress in the art has been advanced by the invention.

What is claimed is:

1. A method of producing a finish for a selected wood substrate, wherein the finish provides the selected wood substrate with a color that matches the color of a target object, said method comprising the steps of:
- providing a spectrophotometer;
- providing a plurality of different colorants, wherein none of the colorants are a white colorant;
- providing a vehicle for producing semitransparent wood stain;
- providing at least one database containing spectral data for the colorants as applied to at least one type of wood;
- obtaining reflectance measurements of the target object using the spectrophotometer;
- performing calculations to determine the quantities of at least one group of the colorants required to produce a semitransparent wood stain from the vehicle, wherein when the semitransparent wood stain is applied to the selected wood substrate, the selected wood substrate will have a color that matches the target object, and wherein the calculations are performed using the spectral data of the colorants and the reflectance measurements of the target object;
- producing the semitransparent wood stain from the vehicle and the at least one group of colorants;
- staining a portion of the selected wood substrate with the semitransparent wood stain;
- obtaining reflectance measurements of the stained portion of the selected wood substrate using the spectrophotometer; and
- determining whether the color of the stained portion of the selected wood substrate is within a certain color tolerance of the color of the target object, wherein the determination is made using the reflectance measurements of the target object and the reflectance measurements of the stained portion of the selected wood substrate.

2. The method of claim 1, wherein if the color of the stained portion of the selected wood substrate is not within the certain color tolerance, the method comprises the following additional steps:
- performing additional calculations to determine quantities of the at least one group of the colorants required to produce a second semitransparent wood stain from the vehicle, wherein when the second semitransparent wood stain is applied to a second portion of the selected wood substrate, the second portion of the selected wood substrate will have a color that matches the target object, and wherein the additional calculations are performed using the spectral data of the colorants, the reflectance measurements of the target object and the reflectance measurements of the stained portion of the selected wood substrate;
- producing the second semitransparent wood stain from the vehicle and the at least one group of colorants; and
- staining a second portion of the selected wood substrate with the second semitransparent wood stain;
- obtaining reflectance measurements of the stained second portion of the selected wood substrate using the spectrophotometer; and
- determining whether the color of the stained second portion of the selected wood substrate is within a certain color tolerance of the color of the target object, wherein the determination is made using the reflectance measurements of the target object and the reflectance measurements of the stained second portion of the selected wood substrate.

3. The method of claim 1, wherein the at least one database comprises a plurality of databases containing spectral data for the colorants as applied to different types of wood, each of said databases being dedicated to one type of wood; and wherein the method further comprises the step of:
- inspecting the selected wood substrate to determine what type of wood it is; and
- selecting the database dedicated to the type of wood that is the same as or closest to the type of wood the selected wood substrate is composed of; and
- wherein the calculations are performed using the spectral data of the colorants from the selected database.

4. The method of claim 1, wherein the reflectance measurements of the selected wood substrate are taken at set wavelength intervals along the visible light spectrum, and wherein the reflectance measurements of the target object are taken at set wavelength intervals along the visible light spectrum.

5. The method of claim 4, wherein the reflectance measurements of the stained portion of the selected wood substrate are average reflectance measurements, each of said average reflectance measurements being an average of localized reflectance measurements taken at a plurality of different locations on the stained portion of the selected wood substrate.

6. The method of claim 5, wherein the localized reflectance measurements of the stained portion of the selected wood substrate are made in at least one light wood area and in at least one dark wood area.

7. The method of claim 6, wherein the localized reflectance measurements of the stained portion of the selected wood substrate are made in two light wood areas and in two dark wood areas.

8. The method of claim 4, wherein the target object is a stained piece of wood and wherein the reflectance measurements of the target object are average reflectance measurements, each of said average reflectance measurements being an average of localized reflectance measurements taken at a plurality of different locations on the target object.

9. The method of claim 8, wherein the localized reflectance measurements of the target object are made in at least one light wood area and in at least one dark wood area.

10. The method of claim 9, wherein the localized reflectance measurements of the target object are made in two light wood areas and in two dark wood areas.

11. The method of claim 1, wherein the target object is a stained piece of wood, and wherein the method further comprises the step of inspecting the target object to determine if it has a clear topcoat, and wherein if the target object is determined to have a clear topcoat, the method further comprises the steps of providing a clear topcoat and applying the topcoat to the stained portion of the selected wood substrate before obtaining the reflectance measurements of the stained portion of the selected wood substrate.

12. The method of claim 1, wherein the calculations are performed using a computer.

* * * * *